United States Patent
McGee

(10) Patent No.: US 9,566,339 B2
(45) Date of Patent: Feb. 14, 2017

(54) SYSTEMS AND METHODS OF USING CHEMICALLY BOUND ANTIBIOTICS ACTIVATED BY INFECTIONS

(71) Applicant: Osteoceramics, Inc., Ames, IA (US)

(72) Inventor: Thomas D. McGee, Ames, IA (US)

(73) Assignee: Osteoceramics, Inc., Ames, IA (US)

( * ) Notice: Subject to any disclaimer, the term of this patent is extended or adjusted under 35 U.S.C. 154(b) by 0 days.

(21) Appl. No.: 14/210,646

(22) Filed: Mar. 14, 2014

(65) Prior Publication Data

US 2014/0274971 A1 Sep. 18, 2014

Related U.S. Application Data

(60) Provisional application No. 61/782,502, filed on Mar. 14, 2013.

(51) Int. Cl.
| | | |
|---|---|---|
| *A61K 47/48* | (2006.01) | |
| *A61K 6/06* | (2006.01) | |
| *A61P 31/00* | (2006.01) | |
| *A61K 31/65* | (2006.01) | |
| *A61K 6/02* | (2006.01) | |
| *A61K 6/00* | (2006.01) | |

(52) U.S. Cl.
CPC ........... *A61K 47/48015* (2013.01); *A61K 6/00* (2013.01); *A61K 6/0265* (2013.01); *A61K 6/06* (2013.01); *A61K 6/0631* (2013.01); *A61K 31/65* (2013.01); *A61K 47/48992* (2013.01)

(58) Field of Classification Search
None
See application file for complete search history.

(56) References Cited

U.S. PATENT DOCUMENTS

| | | |
|---|---|---|
| 5,554,147 A | 9/1996 | Batich |
| 2003/0204229 A1 | 10/2003 | Stokes |
| 2004/0031420 A1* | 2/2004 | Lin et al. .................. 106/35 |
| 2004/0234597 A1 | 11/2004 | Shefer et al. |
| 2004/0247903 A1 | 12/2004 | Axen et al. |
| 2005/0079201 A1 | 4/2005 | Rathenow et al. |
| 2010/0215716 A1 | 8/2010 | Troxel et al. |
| 2013/0209537 A1 | 8/2013 | Fu-Giles |

FOREIGN PATENT DOCUMENTS

| | | |
|---|---|---|
| WO | 2004052339 A1 | 6/2004 |
| WO | 2009131638 A2 | 10/2009 |

OTHER PUBLICATIONS

Ratier et al., Biomaterials, 2001, 897-901.*
Carlotti et al. Phys. Chem. Chem. Phys., 2012, 14, 823-834.*
Ginebra et al., Journal of Controlled Release, 2006, 113, 102-110.*
Pan et al., Crystal Growth & Design, 2010, 10(2), 845-850.*
Pichavant et al., Journal of Controlled Release, 2012, 162, 373-381.*
Dashti et al., Journal of Biomedical Materials Research B: Applied Biomaterials, 2010, 93B (2), 394-400.*
Vahabi et al., Chang Gung Med J, 2012, 35(1), 28-37.*
Stigter et al., Journal of Controlled Release, 2004, 99, 127-137.*
Tsourvakas, Stefanos, Local Antibiotic Therapy in the Treatment of Bone and Soft Tissue Infections, Selected Topics in Plastic Reconstructive Surgery, Dr. Stefan Danilla (ed.), ISBN: 978-953-307-836-6, InTech, 2012, pp. 17-44.
Internatioanl Preliminary Report on Patentability (Chapter I of the Patent Cooperation Treaty). PCTUS2014027096 International filing date: Mar. 14, 2014.
AT-SARX11549-EP—European Search Report dated Sep. 26, 2016.
Tahihara M et al: "A Novel Microbial Infection-Responsive Drug Release System", Journal of Pharmaceutical Sciences, American Pharmaceutical Association, Washington, US, vol. 88, No. 5, May 1, 1999.
Suzuki Y et al: "A new drug delivery system with controlled release of antibiotic only in the presence of infection", Journal of Biomedical Material Research, Wiley, New York, NY, US, vol. 42, No. 1, Jan. 1, 1998.
Yexin Gu et al: "Inkjet printed antibiotic—and calcium-eluting bioresorbable nanocomposite micropatterns for orthopedic implants", Acta Biomaterialia, Elsevier, Amsterdam, NL, vol. 8, No. 1, Aug. 6, 2011.
Bingbing Jiang et al: "Polypeptide nanocoating for preventing dental and orthopaedic device-associated infection: pH-induced antibiotic capture, release, and antibiotic efficacy", Journal of Biomedical Materials Research. Part B: Applied Biomaterials, vol. 88B, No. 2, Feb. 1, 2009.

* cited by examiner

*Primary Examiner* — Abigail Fisher
(74) *Attorney, Agent, or Firm* — Nyemaster Goode, P.C.

(57) ABSTRACT

Methods, devices and systems are disclosed for chemically bonding antibiotics to selected substrate materials which are not dissolved in normal physiological processes so that high local concentrations can be achieved during the inflammatory response. The antibiotics will remain permanently bonded to the substrate material until an infection occurs which releases the antibiotic in high concentrations to help control the infection. The high local concentrations may be much higher than systemic toxic levels, and can never reach toxic levels because the local dose is much less than needed to reach systemic toxicity if completely dissolved.

13 Claims, 2 Drawing Sheets

FIG. 1

Reacting a substrate with an antibiotic to create an antibiotic laden substrate wherein there is a chemical bond between the substrate and the antibiotic Inserting the antibiotic laden substrate into a patient during a medical procedure Maintaining the chemical bond between the substrate and the antibiotic after insertion into the patient under normal physiological conditions Promoting the release of the antibiotic from the substrate upon the occurrence of an infection around the substrate in high concentration to help defeat the infection

FIG. 2

Cementing the femoral component of a hip joint implant with OSTEOCERAMIC antibiotic orthpaedic cement Add about 5-20 volume % of 65 to 270 mesh OSTEOCERAMIC granules that have surfaces coated with one molecular layer of tetracyclineHCl to the cement powder Smear mix the coated granules with about 30 grams of cement powder in a plastic bag to a homogeneous color in blue light Add about 8.2 ml of about 2 m $CaCl_2$ setting solution to a mixing cup and stirring in the powder for about 2 minutes. The mixture will be fluid.

Transfer the fluid to a catheter syringe and deliver it to fill the prepared surgical site.

Insert the femoral component implant, allowing the cement to set, complete the surgical procedure and x-ray the hip The femoral component is now permanently protected by the tetracycline embedded in the cement. If an infection occurs the tetracycline will be released in high concentration to defeat it.

SYSTEMS AND METHODS OF USING CHEMICALLY BOUND ANTIBIOTICS ACTIVATED BY INFECTIONS

This application is based upon U.S. Provisional Application Ser. No. 61/782,502 filed Mar. 14, 2013, the complete disclosure of which is hereby expressly incorporated by this reference.

BACKGROUND

Controlled release of antibiotics has been studied all around the world for use in both systemic and local applications. The rate of release from a carrier system for a wide variety of diseases or infections depends on many factors including carrier solubility, acid-base relationships, structure and porosity of the carrier, mixed carriers of different solubilities to control or extend release rates of the mixture, etc. These are all based on short term release that is usually on days or weeks of release, not on long term protection. Release typically starts at a high concentration and falls off exponentially with time and/or is parabolic with time. Bacteria are constantly evolving so some strains in the mixture will have lower minimum effective concentrations than others. At some point the concentration will fall below the therapeutic level such that those with the low minimum effective concentration will be inhibited but those with the higher minimum effective concentration will survive. The slow rate of antibiotic release below the lower minimum effective release concentration allows the most resistant strains to survive and multiply leading to the development of antibiotic resistant bacteria. High local concentrations of antibiotics are often used but their activity is gone as soon as they are dissipated.

All implants used in surgical repair under load-bearing conditions are walled off by the patient's foreign body response. Examples include, but are not limited to, metals such as 310-L stainless steel, cobalt chrome alloys, titanium alloys; aluminum oxide; polyethylene and polymethylmethacrylate. Local infections sometimes occur after surgery, either from sepsis during surgery or by localization of systemic infections after surgery. For example, *Staphylococcus aureus* may produce a biofilm on the surface of implants that acts as a barrier which prevents antibiotics at systemic levels from curing the infection. Endotoxins are released from Gram-negative bacteria when undergoing autolysis. The endotoxins invoke inflammatory response including local reduction of pH. Resorption of tissue often accompanies these infections.

Many infections associated with orthopedic implants which are difficult to treat systemically are classified as Gram-negative bacteria. They have a tough outer capsule that is resistant to antibiotic penetration. They can secrete cytokines and induce toxic immune responses such as endotoxins. They induce the tissue inflammatory response such as proliferation of monocytes, macrophages, fibroclasts, and osteoclasts that lysis proteins, connective tissue and bone by lowering the pH or by humoral components. This cause redness, swelling and pain and results in resorption of tissue, including bone.

Using orthopedic surgery as an example, but not to exclude other surgical procedures, joint replacements, such as knees or hips, are plagued by "deep infections" where a local infection occurs at the implant site that cannot be cured by systemic antibiotics. About 750,000 knee and hip implants are implanted each year in the United States. About 2% experience deep infection. These are very painful and are accompanied by inflammatory responses that can cause bone resorption and loosening of the implant. This requires removal of the implant, use of systemic antibiotics to cure the infection and allow healing that may require several months, followed by revision surgery to insert a new joint implant. Revision surgeries are more difficult than primary surgeries. There are many other examples such as infection accompanying an open fracture, osteomyelitis, spinal and oral facial surgery.

Other examples occur in dentistry. For example, root canals are required when a tooth becomes infected. If the root canal does not control the infection, the tooth must be removed. Crowns on teeth are cemented in place with luting cement. If the exposed cement at the margins is eroded and caries occurs under the crown, the crown must be removed, the caries damage repaired, a new restoration prepared, and a new crown placed. If periodontal disease occurs sufficient to require debridement of the tooth/or bone, local antibiotics are often administered to prevent re-infection. This may not be successful and the tooth may need to be removed. These examples show the need for a local antibiotic that will be released if infection occurs. There is an urgent need to prevent and/or control local infections in soft and hard tissues.

In studying the mechanisms of tissue response to implants, fluorescent labels may be used to analyze the healing process. Using bone as an example, not to exclude other applications, the fluorescent label is a dye that can be given at a specific time that is absorbed by the bone only at sites where new bone is forming. More than one label can be used at specific times. Then, when the specimen is recovered, sections can be cut from the site of interest and examined with a fluorescent microscope. Each color of fluorescent dye can be visualized so that the precise areas where new bone was forming at the time the dye was given can be mapped. And the spacing between each dye can be used to determine the rate that the bone was forming. This is a powerful tool for understanding bone formation and tissue response.

The tetracycline family of antibiotics is very extensive, all based on four fused hexagonal "Rings" in a linear array, generally in a linear planar construction. When tetracycline was introduced as an antibiotic in the 1940s, it was a wonder drug, broad spectrum to inhibit growth of many bacteria whether gram negative or gram positive, and even inhibited rickettsia diseases like Rocky Mountain Scarlet Fever. There were only about three variants but bacterial resistance developed. Many variations of tetracycline have been developed to improve performance. But the resistant strains have limited its use. The simplest form is shown in Diagram 1 as a planar molecule. The rings are labeled A B C D and the branches off the rings appear to be in the plane also. Actually, in the three dimensions the branches are kinked so that extensions off the A ring look like bent thumb and index fingers. The spacing is steric (correct geometry) for chelating a calcium ion (as though the ion was caught in the fingers grasp). This is held tightly as a strong chemical bond composed of steric, covalent and ionic components. When this happens the molecule is no longer effective as an antibiotic. The bond is difficult to break.

The original tetracycline was infused (welcomed into) bacteria cells where it interfered with the ribosomes that manufacture proteins for cell multiplication. Resistance by bacteria includes modifications that pump the tetracycline out of the cell before it can interfere with the protein manufacture; or modify the ribosome RNA to allow manufacture of proteins in the presence of tetracycline.

Diagram 1—Basic structure of the simplest tetracycline

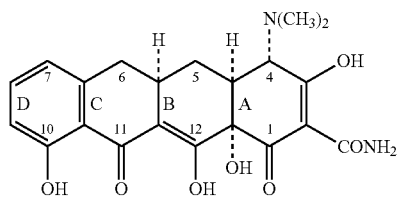

Ciprofloxacin is a member of the quinolone family of drugs. Early quinolones were not as effective as the fluoroquinolones. Ciprofloxacin is a second-generation fluoroquinolone antibiotic that had a wide spectrum of applications in clinical use in the 1980s and 1990s. In 2000 it was the fifth most commonly prescribed drug in the U.S. Increased resistance and the structure of the molecule (Diagram 2) allow many variants to be investigated. In general the improved drugs avoid some of the mechanisms for antibiotic resistance and research is still being conducted. There are now thousands of derivatives.

Ciprofloxacin prevents bacteria growth by targeting two essential bacterial enzymes, DNA gyrase and DNA topoisomerase IV that are essential to cell reproduction. The quinolones bond to aluminum ions by a chelating complex similar to the bonding of calcium ions to tetracycline described above. The bond is very stable and prevents antibiotic activity.

Diagram 2—Basic structure of Ciprofloxacin

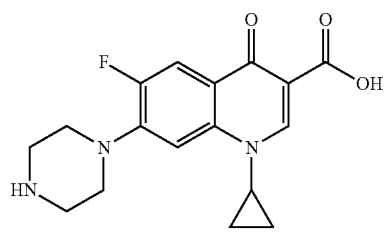

SUMMARY

The present invention relates to devices, systems, processes, and methods for binding a biologically active agent such as an antibiotic to a biologically active substrate material for controlled activation and release of the active agent after the substrate material has been placed into a patient's body. The biologically active substrate materials may include inorganic or organic compounds that are suitable for applications such as orthopaedic, spinal, dental and veterinary surgeries Two suitable biologically active agents are the antibiotics tetracycline and ciprofloxacin. Tetracycline and ciprofloxacin (cipro) develop strong bonds on suitable biologically active substrates by a chelating mechanism. Each of these antibiotics has a certain location on its chemical formula where both electrostatic charge on the ion and the size of the ion in the substrate is just right to form a strong chemical bond. It is as though the structure bites the ion to hold it tightly. Because these are such strong bonds, they are permanent. The antibiotic is rendered inactive for pharmaceutical purposes upon attachment to the substrate material. It remains attached to the binding site and is fixed permanently to the substrate until an infection or an inflammatory response occurs. Then the substrate to which the antibiotic is bound is dissolved, freeing the antibiotic to be active again. This may occur at the time of surgery as the result of the inflammatory response during wound healing, a desirable feature because it prevents infection immediately after surgery. This does not deplete the reservoir of antibiotic available for later release when infection triggers the release.

Release of the antibiotic also can result for infections that are the result of systemic infections that localize sometime after surgery at an implant site. These deep infections are serious. Preventing them with an antibiotic that will be released if an infection occurs is very desirable.

Wide spectrum antibiotics are desirable for a wide range of diseases. High local concentrations are not subject to the toxic limits of systemically administered antibiotics. The quantity needed for high local concentration is too small to exceed the systemic toxic limit.

Descriptions and examples will be based on research which was performed in the orthopaedic and dental fields, but the invention is applicable to all types of tissues for many infectious diseases; so the dental and orthopedic applications are to be taken as examples and not to limit the scope of the invention. Any antibiotic that can be chemically bound to a useful substrate which is insoluble in the normal physiological environment, but can become soluble in the physiological environment induced by a disease is a suitable candidate if the antibiotic retains its properties when it is released. The mechanism can be explained with reference to the following examples.

EXAMPLE 1

Tetracycline is used herein as an example but not to limit the scope of the invention. The tetracycline family of antibiotics is very large and many tetracycline antibiotics are used to treat a variety of infections. In one embodiment, tetracycline is permanently chemically bound to a substrate material containing calcium, such as the substrate materials disclosed in U.S. Pat. Nos. 3,787,900; 6,312,467; 6,364,909 and 6,719,793, the contents of which are incorporated herein by this reference. These patents disclose biologically active substrate materials comprising tricalcium phosphate to control tissue response and either magnesium aluminate or calcium aluminate to obtain enduring strength. Both tricalcium phosphate and calcium aluminate are used in a hydraulic cement to provide enduring strength in the latter patent. The materials disclosed in these patents are sold under the brand name OSTEOCERAMIC. After chemically binding the tetracycline to the substrate material, the antibiotic laden substrate material is then inserted into the patient where it remains bound to the substrate material until it is released by the patient's response to an inflammatory response at the time of surgery or by an infection at the site of the substrate.

The normal pH in tissue environments is about near neutral, about 6.0 to 7.5. pHs as low as 2-5 are often present for bone and protein lysis. Cells such as monocytes, macrophages, fibroclasts and osteoclasts are examples of cells that produce low pH that will dissolve tricalcium phosphate and release the antibiotic. But enzymes and many other bioactive humoral components that destroy the chemical compound without destroying the antibiotic are candidates for the release of the antibiotics and are included in the scope of this patent.

The composition of the substrate material to which the antibiotic is bound is limited by both the antibiotic and the compounds suitable for developing a stable bond in normal physiological conditions and the release of the antibiotic, still effective, by the presence of an infection. For tetracycline the bond depends on calcium salts that have the required properties just described. Suitable salts could be other calcium phosphates and other calcium compounds or alkaline earths, including zinc oxide, if they are useful for applications as implants. Orthopedic implants must have enduring strength to be functional in load bearing situations. For void filling the choice of compounds is wider. Many calcium salts that are too soluble for functioning as load bearing become available for void fillers or soft tissue applications and all are within the scope of this invention. When the substrate is a solid body implant, maximum utility is gained by an implant that has load-bearing properties such as the OSTEOCERAMIC implants disclosed above. In addition to solid body implants, other types of substrate materials may be used, including granular cements and void fillers which may include calcium phosphates, hydroxyapatite, fluoroapatite, cancellous bone, and cortical bone from cadavers. Calcium salts such as calcium sulfates and calcium aluminates are possible candidates as well. In some embodiments an antibiotic laden solid body implant may be used along with an antibiotic laden granular cement and/or void filler in the same medical procedure.

Calcium ions at the surface of a solid will react with tetracycline by a chelating reaction where the positive Ca ion is trapped in a tooth-like cavity of the antibiotic that has a negative charge. Chelating reactions are special reactions that induce both electrical charge and geometry to produce a bond that is very stable. The chemical bond is stable at the usual pH of functional bone and the tetracycline is permanently bound until an inflammatory response or an infection occurs. An infection causes a drop in pH and/or other humoral mechanisms for lysis that releases the tetracycline at very high local concentrations. If the compound is dissolved by an acid, the source of stability of the calcium salt is lost and the active tetracycline is released from the substrate material to fight the infection.

EXAMPLE 2

Ciprofloxacin is used herein as an example but not to limit the scope of the invention. The fluoroquinoline family of antibiotics bonds to aluminum ions. Ciprofloxacin is representative of that family. Ciprofloxacin can be chemically bound to any suitable substrate material, including the OSTEOCERAMIC cement disclosed in U.S. Pat. No. 6,723,334, the contents of which are incorporated herein by this reference. During the cement setting process aluminum chlorohydrates and aluminum hydroxide $[Al(OH)_3]$ is formed to which the ciprofloxacin bonds. The cipro bond displaces the hydroxyls to bond to the aluminum ion. The bond is stable until the physiological pH and other mechanisms of lysis caused by wound healing or an infection release the ciprofloxacin by dissolving the cement hydration products. Experimental culture studies verify that ciprofloxacin controls the infection. It is still effective as an antibiotic on release. Note also that the aluminum hydroxide may be effective against the endotoxins accompanying bacterial infections.

Both of these examples show embodiments of the present invention wherein broad spectrum antibiotics are permanently bound to substrate materials, remaining dormant in high concentrations at a local site until an infection occurs to release the antibiotic that destroys the infection. Because the concentrations are much higher than is possible by systemic methods, the high-resistance fraction of the bacteria culture should be destroyed.

BRIEF DESCRIPTION OF THE DRAWINGS

FIG. 1 is a flowchart showing an exemplary method of using the invention; and
FIG. 2 is a flowchart showing another exemplary method of using the invention.

DETAILED DESCRIPTION

The present invention relates to devices, systems, processes, and methods for binding a biologically active agent such as an antibiotic to a biologically active substrate material for controlled activation and release of the active agent after the substrate material has been placed into a patient's body. The biologically active substrate materials may include organic or inorganic compounds as a part of or bonded to cements, implants, implantable hardware, void fillers and soft tissue wounds. In one embodiment, the invention is a method for controlled antibiotic release wherein a selected antibiotic is chemically bonded to an implant or other substrate material in such a way that it will be released if a bacterial infection occurs after insertion into the patient. It may also be released by an inflammatory response to a wound as in the initial implant surgery. The infection and inflammatory response cause a drop in pH and/or other humoral mechanisms of lysis which release the antibiotic from its chemical bond. In one embodiment, the antibiotic remains permanently bonded to the substrate at a pH of above about 7.0 and the chemical bond is broken when the pH drops below about 5.0 upon the occurrence of a local infection near the substrate to activate the antibiotic and fight the local infection. The antibiotic concentrations are much higher than the systemic toxic limit, and thereby help to cure the infection. The controlled activation and release of the active agent serves as a drug delivery system to fight infections which may occur during and after a medical procedure.

The bonding of the antibiotic to the substrate is a chemical reaction that can vary with the reactants. When the antibiotic is soluble and the substrate is a solid implant the antibiotic can be dissolved in the fluid, typically aqueous, and the solid implant can be immersed in the solution to allow the reaction to take place at the surface. Conditions of concentration, temperature, and stirring are needed. After the reaction is complete the implant can be rinsed and dried. If the implant is made of particles the same basic reaction can take place on the surface of the particles. In one example below the tetracycline is bonded to the exterior of solid orthopaedic implants containing tricalcium phosphate, and in another example it is bonded to particles of tricalcium phosphate powder that are one component of the orthpaedic cement powder. For ciprofloxacin in the cement the antibiotic powder can be incorporated with calcium aluminate cement in the dry powder mixture. The setting liquid will be added during surgery. Also for ciprofloxacin in the cement the cipro can be dissolved in the setting liquid for use during surgery. In both cases the setting reaction and the bonding to the implant occur during setting.

Many other chemical reactions and mechanisms of incorporation are possible. The examples are not to be considered to limit the scope of the invention.

FIG. 1 shows the general method steps for practicing an embodiment of the invention. First, the substrate is chemically combined with a biologically active agent such as an antibiotic to create an antibiotic laden substrate. The substrate is then inserted into a patient during a medical procedure. The chemical bond between the substrate and the antibiotic remains under normal physiological conditions but breaks upon the occurrence of an infection around the substrate. The breakage of the bond releases a high local concentration of antibiotic to help fight the infection.

FIG. 2 shows a more specific embodiment of the invention wherein an OSTEOCERAMIC cement substrate material is combined with tetracycline then used in the cement for a hip joint implant.

EXAMPLE 1,CONTINUED

Tetracycline creates a permanent chemical bond with the calcium in hydroxyapatite, the mineral in bone. Tetracycline also creates a permanent bond with the tricalcium phosphate in the biologically active OSTEOCERAMIC materials. For this reason, OSTEOCERAMIC disks were selected for the first experimental evaluation. Although OSTEOCERAMIC brand disks were selected for this experiment, it is apparent that any suitable substrate material containing tricalcium phosphate, hydroxyapatite, cortical bone, other calcium phosphates and other calcium compounds or alkaline earths could be selected if they are useful as implants.

A.) First, experimentation was done to determine whether tetracycline will bond to OSTEOCERAMIC grafts. Disks 10 ml diameter by 1 mm thick were made. Tetracycline HCl tablets were crushed and aqueous solutions of 0.01, 0.1, 1.0 and 10.0 mg/ml concentration were made. Disks were exposed to these solutions while supported on plastic mesh and stirred at room temperature for 24 hours while shielded from the light. They were rinsed with deionized water and dried. The surface of the disks was colored a light orange that increased in proportion to the concentration of the tetracycline solution. The rate that coloration occurred also increased with concentration. The disks fluoresced in near ultraviolet light at intensities proportional to the concentration. Specimens were rinsed in deionized water four times for eight hours; and also in lactated Ringers solution that is used to simulate body fluids, to see if the rinsing would remove the tetracycline. The solutions were saved for bioactivity testing. The tetracycline bonded to the disks and was not soluble in the wash liquids based on the experiments explained below.

B.) The affect of chemical agents on bacteria was evaluated using the Kirby-Bauer method in which petri dishes of Mueller-Hinton agar were coated with a selected bacterium. The tetracycline coated disks were pressed lightly on top of the bacteria-coated agar. The dishes were incubated at 35° C. in a controlled atmosphere for 24 hours. In this method the plates covered with agar are each seeded with a specific bacterium. Note that the Kirby-Bauer method has both positive and negative controls. The positive control is a paper disk containing a standard amount of a specific antibiotic. The negative control is a substrate disk without any antibiotic. Disk shaped specimens are put on the agar well space apart. During the culture time the bacterium grows and discolors the agar wherever it has grown. If growth of bacteria by an antibiotic, then the plated agar results were scored for the radial length of the zone of inhabitation of bacterial growth around the disks. The rinse solutions from part A above were used to wet sterile paper disks and tested in the same manner. The rinse solutions and the disks without tetracycline did not inhibit bacterial growth. The OSTEOCERAMIC disks coated with the tetracycline at concentrations of 0.01 mg/ml solution and above did inhibit bacterial growth. Those made with concentrations of 1 and 10 mg/ml were effective in creating large inhibition zones.

Because tooth roots are in an anaerobic environment, bacteria were selected from those commonly encountered in periodontal disease for evaluation by the Kirby-Bauer method. They were ATCCJ177i: *Bacillus cereus, Corynebacterium* spp., *Esccherichia coli, Pasteurella multocida* and *Staphylococcus* spp. Each was doped on Mueller-Hinton agar at $10^4$ to $10^6$ levels. Bacterial growth was prevented adjacent to the disks treated with 0.1 mg/ml, 1 mg/ml and 10 mg/ml. Rinse solutions did not inhibit growth indicating that the tetracycline bonded to the substrate and did not come off with the rinse solution.

Dental and bone labeling evidence demonstrates that the tetracycline bonded to calcium in tooth and OSTEOCERAMIC implants are permanent and harmless to tissue. The Kirby-Bauer evaluation of wash solutions shows that the antibiotic, tetracycline HCl, is not released when no infection is present and that infection is inhibited adjacent to the implant when it is present. Other experiments have verified that democlotetracycline and oxytetracycline are also effective. The tetracycline coated implant becomes a "smart" implant such that antibiotic is only released when an active infection occurs. No inflammatory response is involved in the culture reactions so the bacteria induced the tetracycline release. The control did not inhibit the bacteria.

The concentration of tetracycline in the solutions used to transfer tetracycline to the disks is known, 0.1, 1.0, and 10.0 mg/ml. The amount actually transferred to the disks is unknown. The surfaces of the disks were altered in color as the concentration increased but it did not penetrate into the bulk of the disks. The amount of tetracycline released from the disks is unknown but it was enough to inhibit the bacteria in large zone around the disks. We can estimate the surface load if we assume that the surface concentration is equal to one tenth the solution concentration:

The surface area of the disk is equal to $nDt+2\pi r^2$ where the diameter (D) is 9 mm, the radius (r) is 4.5 mm, and the thickness (t) is 1.5 mm.

$$\begin{aligned}\text{The surface area} &= \pi(9)(1.5) + 2\pi(4.5)^2 \\ &= \pi[13.5 + 40.5] \\ &= 54\pi \\ &= 169.7 \text{ mm}^2\end{aligned} \quad 1.$$

$$\begin{aligned}\text{Tetracycline on the surface} &= 169.7 \text{ mg/mm}^2 \, (0.01), (0.10), \\ &\quad (1.0) \text{ mg/mm}^2) \\ &= 1.69, 16.9, \text{ and } 169\end{aligned} \quad 2.$$

3. The systemic dose limit, at 500 mg/kg maximum for a 45 kg person is 500/4500=0.011 mg/gm.
4. The ratio of chemically bound tetracycline to the maximum systemic dose is:

$$1.69/0.011; \; 16.9/0.011; \; 169/0.11 = 6.48; \; 64.8, \text{ and } 648$$

This local concentration is for more than the systemic limit so the amount of tetracycline released at the infection can be much greater than the systemic dose. If the entire maximum dose that was delivered to the surface, 169 mg, were released instantaneously, it is much less than the 500 mg systemic maximum so that maximum can never be exceeded.

EXAMPLE 2, CONTINUED

The quinolones react with aluminum salts. There are many different antibiotics based on the quinolones including the ciprofloxacin family. Because it has a wide spectrum of bacterial applications, and is effective at low concentrations, ciprofloxacin was chosen for example 2 in which it was bonded to aluminum ions in the OSTEOCERAMIC bone cement disclosed in U.S. Pat. No. 6,723,334. The OESTOCERAMIC dry cement powder comprises tricalcium phosphate and calcium aluminate. Although OSTEOCERAMIC brand disks were selected for this experiment, it is apparent that any suitable substrate material containing aluminum ions may also be used. The calcium aluminate cement reacts with a 2 molar calcium chloride aqueous setting solution to produce calcium alumino-chlorohydrate and aluminum hydroxide. The hydrated calcium aluminate is biocompatible with soft and hard tissues. Both hydration products react with ciprofloxacin, although the aluminum hydroxide may dominate. The calcium phosphate is more soluble than the calcium aluminate hydration products. The calcium phosphate controls the tissue response and the hydrated calcium aluminum cement products provide rapid setting and enduring strength. OSTEOCERAMIC cement has been used to fix canine hips in place. It has many potential orthopedic, spinal and dental applications.

Experiments with 500 mg cipro tablets were conducted to determine how the cipro could be added to the cement. The powder portion of the cement is composed of both tricalcium phosphate powder and calcium aluminate cement powder. The setting solution is aqueous calcium chloride. First powdered cipro was added to the cement powder; then the tablets was dissolved in the setting solution. Both methods were suitable. In Example 2 Ciprofloxacin was added to the setting solution (it does not bond to calcium ions) in concentrations of $10^{-4}, 10^{-3}$, and $10^{-2}$ gr/gram of calcium aluminate in the OSTEOCERAMIC cement powder. The powders were added to the setting solution and mixed for 1 to 2 minutes and the mixture was cast into molds to produce disks about 9 mm diameter by 1-2 mm thick. After setting, the disks were removed from the molds and transferred to sealed centrifuge vials containing 30 ml sterile saline and agitated for selected time periods in a 37° C. water bath. After rinsing, there bioactivity was evaluated by the Kirby-Bauer method using Mueller-Hinton agar for 24 hours at 35° C. Plates of agar were doped with *Escherichia Coli*, *Staphylococcus aureus*, or *Psuedomonus aeruginosa*. Data were collected for one hour, one day, and one week after setting as shown in tables 1, 2, and 3.

TABLE 1

Kirby-Bauer Inhibition Zone
*E. Coli*

| Concentration | 1 Hour | 1 Day | 1 Week |
|---|---|---|---|
| $10^{-4}$ | 34 mm | 22 mm | 23 mm |
| $10^{-3}$ | 42 mm | 27 mm | 33 mm |
| $10^{-2}$ | 49 mm | 37 mm | 44 mm |

TABLE 2

Kirby-Bauer Inhibition Zone
*Staph. A.*

| Concentration | 1 Hour | 1 Day | 1 Week |
|---|---|---|---|
| $10^{-4}$ | 7 mm | 0 mm | 0 mm |
| $10^{-3}$ | 27 mm | 5 mm | 21 mm |
| $10^{-2}$ | 34 mm | 29 mm | 32 mm |

TABLE 3

Kirby-Bauer Inhibition Zone
*Pseudo. A.*

| Concentration | 1 Hour | 1 Day | 1 Week |
|---|---|---|---|
| $10^{-4}$ | 21 mm | 0 mm | 0 mm |
| $10^{-3}$ | 34 mm | 19 mm | 21 mm |
| $10^{-2}$ | 44 mm | 35 mm | 39 mm |

These results indicate that at concentrations of $10^{-2}$ grams ciprofloxacin per gram of calcium aluminate the inhibition is effective for one week for all three bacteria. This too is a smart material.

In this example, the precise concentration of the antibiotic in the bulk of the hydrated cement is known but the amount of antibiotic released in the Kirby-Bauer test is unknown. However, it was enough to prevent bacteria growth in a large zone around each disk.

The amount of ciprofloxacin in the cement can be compared to the systemic limit. As before, using a 45 kg patient (100 lbs) and 1000 mg at 12 hour intervals as the maximum dose, 1000/4500 g=0.02 mg/gm Chemically bound: 500 mg in 15 grams of cement powder 500/15=33 mg/gm Ratio: 33/0.02=1600 times higher local concentration than the systemic limit. The cement, after setting is dense so the interior is not accessible unless exposed. The amount released from the surface in the Kirby-Bauer tests is unknown but it is enough to be effective. If the entire amount was released, it would be only one half the systemic limit.

Broad spectrum antibiotics are desirable and combinations of antibiotics are often used to combat resistant diseases. Because the OSTEOCERAMIC cement contains tricalcium phosphate, calcium aluminate cement, and calcium aluminate cement hydration products, it is possible to include both tetracycline and the quinolones in the same implant structure to increase the antibiotic spectrum.

EXAMPLE 3

Pellets of the OSTEOCERAMIC bone graft material described in example 1 were crushed to produce particles. These were separated into sizes with sieves, to produce a range of size fractions; 12-20 mesh, 20-35 mesh, 35-65 mesh, 65-270 mesh, and minus 325 mesh. Each of these fractions was treated with an amount of tetracycline HCl needed to convert the surface to chemically bound tetracycline. The tetracycline bonds to the tricalcium component of the grain surfaces. The microstructure of the OSTEOCERAMIC bone graft is like a sponge with the holes in the sponge filled with solid tricalcium phosphate. So the tricalcium phosphate phase is interconnected throughout the volume and is exposed at 50% of the surface area. The finer grain-sized particles have larger surface area per gram so more tetracylcline can be bound to the finer particles Attachment was achieved by immersing each size fraction in aqueous tetracycline solution sufficient for a monolayer to be produced on the surface of the particles. The surface area was calculated assuming the particles were spheres of the median radius for the sieve fraction. The tetracycline molecule was assumed to be 24 $A^2$ in binding cross section. The grains changed from white to orange as a result of the treatment. These grains were used to make cements for filling bone voids, combining 65% of one fraction with 15% of the second, finer, fraction in the series, 5% of the −325 mesh fraction and 15% of cement. Different cements were used, including gypsum, calcium aluminate and zinc phosphate cements. These concretes set in 5 to 10 minutes in a wet environment. After curing 24 hours at 100% humidity and 37° C., disks of these concretes were tested in Mueller-Hinton agar cultures to determine if they would inhibit bacterial growth. They were found to perform in the same way as the disks in example one. Thus the concrete prostheses have the properties needed to treat bone voids. Note that the size of the coarse fraction 12-20, 25-35 or 35-65 will depend on the maximum particle size that must not exceed the maximum size of the void to be filled.

EXAMPLE 4

A Kirby-Bauer test using *staphylococcus aureus* was repeated for ciprofloxacin-doped cement with more detail. All specimens, and the paper control, were 6 mm diameter.
*Staphylococcus* A. Results

| Identity | Zone size, mm |
| --- | --- |
| 5 mg control | 42 × 56 |
| Cement, NO cipro | 0 × 0 |
| $10^{-2}$ g/g, rinsed | 46 × 46 |
| $10^{-2}$ g/g, rinsed | 46 × 46 |
| $10^{-3}$ g/g, rinsed | 31 × 32 |
| $10^{-3}$ g/g, rinsed | 20 × 22 |
| $10^{-2}$ g/g, not rinsed | 51 × 42 |
| $10^{-2}$ g/g, not rinsed | 46 × 42 |
| $10^{-3}$ g/g, not rinsed | 49 × 42 |
| $10^{-3}$ g/g, not rinsed | 47 × 42 |

From these results, the $10^{-2}$ g/g concentration was equivalent to the control disk. $10^{-3}$ g/g was somewhat less. The cement without ciprofloxacin had no antibiotic effect. Rinsing the pellet to remove surface antibiotic had no effect. The normal pH in tissue environments is about 7.3, although pHs as low as 3 are often present for bone and protein lysis. Cells such as monocytes, macrophages, fibroclasts and osteoclasts are examples of cells that produce lysis by low pH. But enzymes and many other bioactive components that destroy the chemical compound without destroying the antibiotic are candidates for the release of the antibiotics and are included in the scope of this patent. Note that the Kirby-Bauer results indicate effective inhibition zones are not always the result of pH change alone because staph does not reduce the pH. Other, unknown factors must be responsible in some cases.

Bone void fillers often containing tricalcium phosphate to enhance the healing rate. Example 3 explains that particles of the OSTEOCERAMIC can be processed to provide desired grain sizes. The finer particles have more surface area so they can have more tetracycline. The bound tetracycline can have concentrations more than 1000 times the systemic limit. This can also be done with sintered tricalcium phosphate and tricalcium phosphate. These can be delivered to the trauma site to both enhance healing and treat infections. Mixtures of treated grains with untreated grains can be made to adjust the antibiotic concentration to control the amount of bound tetracycline exposed in the wound. This can be delivered to wound openings, to as deep as the open fracture clot, to be released during the wound healing period. Delivery can be in the form of a powder, or in a liquid suspension or as a plastic mass. The plastic mass can be subdivided to treat local areas. The basic technology to produce these products was described in example three.

The examples set forth above should not be taken as limiting and other antibiotics are candidates for bonding to other suitable substrate materials. Note that for the cements, much more tetracycline is bonded because the particles have tetracycline on all surfaces within the volume of the implant, not just the exterior surfaces (as in the solid body implant embodiments). The examples are to explain application of the invention and are not to be taken as limiting. Many antibiotics are candidates, especially those that must not be taken with other drugs or foods because they will bond to the drugs or foods and become ineffective in the bound form. The examples here are taken from OSTEOCERAMIC inorganic materials for orthopedic, spinal, and dental applications but the theory is applicable to organic, metal and polymer materials.

Many other antibiotics are within the scope of this invention even though only two antibiotic families are identified in the examples. Tetracycline bonds to calcium and ciprofloxacin bonds to aluminum. The antibiotics referenced herein bond to inorganic compounds. However, the principle is general so any antibiotic that binds to organic substrate materials, such that they are stable in the tissue environment and can be released by infection, are also candidates for high, local concentrations.

Applications of the Invention

Many applications of the present invention are possible in many different areas where infection must be controlled. One of the largest is the dental area where the oral cavity is not sterile and endodontics are frequently exposed to bacteria. Many orthopedic surgeries have special antibiotic needs also.

A. Root Canals

Root canal surgery is necessary when a tooth becomes infected. It is often accompanied with an abscess. Systemic drugs often are ineffective. Drills and broaches are used to remove pulp and nerves from the root canal and the canal is packed with gutta-percha mixed with a radiopaque powder. If the infection is not controlled, extraction is required. To improve existing techniques, a highly fluid OSTEOCERAMIC cement is mixed with tetracycline or cyprofloxacin, or both, for example, to fill the root canal and a small adjacent region the apex. This should cure the infection and prevent reinfection from occurring. The tetracycline can bond to the calcium phosphate in the cement and the ciprofloxacin can bond to the hydration products of the calcium aluminate cement. An infection releases the antibiotics by creating an acidic environment which breaks the chemical bonds between the antibiotics and the substrate. Added advantages are the higher strength and better fluidity and lack of shrinkage that occurs when replacing the product with OSTEOCERAMIC cement with antibiotic. OSTEOCERAMIC cement is naturally radiopaque, another advantage. The high fluidity allows it to flow into extremely small holes. If necessary, the surgical procedure can be modified to better prepare the root canal and apical surroundings.

B) Void Filling

Example three demonstrates that grains of various sizes of the substrate material can be covered with chemically bound tetracycline. This will also be true for grains of aluminum oxide that are treated to have aluminum hydroxide surfaces. So the quinolones can also be permanently bonded to aluminum oxide grains unless or until an infection occurs. This makes it possible to make strong, dense, void-fillers by controlled grain size packing of grains held together by a matrix suited to the application. The matrix can be very strong with binders such as OSTEOCERAMIC cement, or it can be biocompatible plasticizers that allow the grains to be packed into an irregular void to be absorbed later and filled in a bioconductive manner with new bone. The size of the void, then, can be accommodated by using coarse grains for large voids and tiny grains for narrow voids. The choice of the antibiotic for the grains and for the matrix can be adjusted to fit the medical requirements. Other applications include filling periodontal lesions where bone and/or teeth infections have been debrided and filling voids in bones after osteomyelitis or cancer treatment.

C) Stabilizing Surgically Created Voids where Bone has been Elevated for Biomechanical Reasons, Such as Tibia Tuberosity Advancement.

The Tibia Tuberosity Advancement surgical procedure is one in which the tuberosity of the tibia is elevated at the proximal end to improve the performance of knee that has as weakened or torn anterior cruciate ligament (ACL). The tibia is the shin bone that has, at the proximal end, a narrow raised swelling to which the tendon for the patella (knee cap) is attached. Severing the tuberosity from the tibia allows the proximal end to be moved forward (advanced) and held in place a metal component that holds that end at the correct position. In that position the forces on the patella tendon help to keep the joint from sliding under stress. With the distal end held at its normal position a wedged shaped void is produced. Healing and filling the void takes many weeks and the procedure is plagued with infection. Filling the void at the time of surgery with a bone graft, a cement or a moldable void filler may shorten the healing time and the antibiotic antibiotic may prevent infection.

D) Stabilizing Artificial Tooth Roots

Titanium alloy tooth roots are placed deep in dense cortical bone of the mandible or maxilla to get strong anchorage. One of the concomitant problems is bone resorption because of localized infections at the junction of the implant and the dense bone. This can be progressive and difficult to treat and is detrimental to implant stability. Use of antibiotic bone cement as discussed above has the advantages of replacing the lost interfacial bone with strong cement which is able to cure and prevent infections.

E) Prevention of Deep Infections

Joint replacements and spinal surgery have inherent dangers of local deep infections that can be resistant to antibiotics. Current practice includes systemic antibiotics before, during, and after surgery; local antibiotics such as gentamicin are often included in polymethylmethacrylate (PMMA) cement. The powder on the surface gives temporary protection but antibiotic grains within the PMMA are buried and not accessible. Where infection may be expected, as in revision of a deep infection implant, strings of beads of PMMA or calcium phosphates, impregnated with an antibiotic such as gentamiacin may be used at the site. The PMMA must be removed and is only effective for a short time. The protection of the calcium phosphate beads lasts only until the beads dissolve. Protection with the current invention is superior to current practice for the reasons discussed above.

The implant can be made from any suitable substrate graft and the components can be cemented in place with any suitable substrate cement. The graft can include antibiotics from the tetracycline family. The cement can include antibiotics from the tetracycline family or the ciprofloxacin family, or both. The antibiotic will be local, high concentration and will not be released unless an infection occurs.

F) Osteoporotic Bone

Osteoporotic bone is often found in orthopedic and dental applications. (Spinal applications can be classified as orthopedic in the sense that both involve osteoporosis.) The osteoporosis weakens the bone and makes surgical repair more difficult. It is often associated with weak immune systems and infection. Use of substrate cement bound with antibiotics to fill pores and strengthen the bone will establish infection control.

G) Open Comminuted (Shattered) Fractures of Bones

Often in severe trauma the bone is badly comminuted and often the wound is open to the surface, so infection is a hazard. The best treatment may be to use external fixation to hold the distal part in alignment with the proximal part and to not disturb the clotted wound, even though there is an opening in which infection could occur. There is an urgent need for a way to enhance the rate of recovery and to control the infection.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

Therefore I claim:

1. A drug delivery system comprising:
a biologically active antibiotic chemically bonded to a biologically active substrate with a chemical bond, the substrate adapted for insertion into a patient during a medical procedure, wherein the substrate comprises tricalcium phosphate and at least one of magnesium aluminate and calcium aluminate, and wherein the antibiotic is one of a tetracycline and a ciprofloxacin;
wherein the substrate is insoluble in a normal physiological environment where no infection or inflammatory response is present and wherein the antibiotic remains inactive for pharmaceutical purposes as long as the substrate is insoluble;
wherein at least a portion of the substrate becomes soluble and dissolves releasing the antibiotic from the substrate by breakage of the chemical bond upon the occurrence of a local infection near the substrate.

2. The system of claim 1 wherein the substrate is a solid body implant.

3. The system of claim 1 wherein the substrate is a particulate body material.

4. The system of claim 1 wherein the antibiotic is released from the substrate when the pH near the substrate is lowered to become more acidic.

5. A method of using a drug delivery system, said method comprising:
chemically bonding an antibiotic to a biologically active substrate with a chemical bond wherein the substrate comprises tricalcium phosphate and at least one of magnesium aluminate and calcium aluminate, and wherein the antibiotic is one of a tetracycline and a ciprofloxacin;

wherein the substrate is insoluble in a normal physiological environment where no infection or inflammatory response is present and wherein the antibiotic remains inactive for pharmaceutical purposes as long as the substrate is insoluble;

inserting the substrate into a patient during a medical procedure;

wherein at least a portion of the substrate becomes soluble and dissolves releasing the antibiotic from the substrate by breakage of the chemical bond upon the occurrence of a local infection near the substrate.

6. The method of claim 5 wherein the substrate is a particulate body material.

7. The method of claim 5 wherein the antibiotic is released from the substrate when the pH near the substrate is lowered to become more acidic.

8. The method in claim 5 where the antibiotic is released from the substrate by the action of enzymes or other humoral components.

9. The method of claim 5 wherein the substrate is a solid body implant.

10. A method of using a drug delivery system, said method comprising:

chelating an antibiotic to an insoluble substrate, wherein the substrate comprises tricalcium phosphate and at least one of magnesium aluminate and calcium aluminate, and wherein the antibiotic is one of tetracycline and ciprofloxacin;

wherein the antibiotic is inactive for pharmaceutical purposes while bonded to the substrate and while in a pH environment of between about 6.0 to 7.5;

inserting the substrate into a patient during a medical procedure;

wherein at least a portion of the substrate becomes soluble and dissolves releasing the antibiotic from the substrate when the pH near the substrate lowers to 5.0 or less during the presence of an infection or inflammatory response, whereby the antibiotic is thereby activated to fight the local infection.

11. The method of claim 10 wherein the substrate becomes insoluble and the antibiotic is inactive for pharmaceutical purposes when the pH rises from 5.0 or less to between about 6.0 and 7.5.

12. A method of using a drug delivery system, said method comprising:

chelating an antibiotic to an insoluble substrate, wherein the substrate comprises tricalcium phosphate and at least one of magnesium aluminate and calcium aluminate, and wherein the antibiotic is one of tetracycline and ciprofloxacin;

wherein the antibiotic is inactive for pharmaceutical purposes while bonded to the substrate and while in a pH environment of between about 6.0 to 7.5;

inserting the substrate into a patient during a medical procedure;

wherein at least a portion of the substrate becomes soluble and dissolves releasing the antibiotic from the substrate by enzyme and humoral mechanisms in the presence of an infection or inflammatory response, whereby the antibiotic is thereby activated to fight the local infection.

13. The method of claim 12 wherein the substrate becomes insoluble and the antibiotic is inactive for pharmaceutical purposes when the infection is no longer present and the enzyme and humoral mechanisms cease.

* * * * *